United States Patent
Hebig et al.

(10) Patent No.: US 9,908,989 B2
(45) Date of Patent: *Mar. 6, 2018

(54) RECYCLATE VERIFICATION

(71) Applicant: International Business Machines Corporation, Armonk, NY (US)

(72) Inventors: Travis R. Hebig, Rochester, MN (US); Joseph Kuczynski, North Port, FL (US); Steven R. Nickel, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 83 days.

This patent is subject to a terminal disclaimer.

(21) Appl. No.: 14/682,147

(22) Filed: Apr. 9, 2015

(65) Prior Publication Data

US 2016/0202233 A1 Jul. 14, 2016

Related U.S. Application Data

(63) Continuation of application No. 14/596,324, filed on Jan. 14, 2015.

(51) Int. Cl.
*C08K 5/092* (2006.01)
*G01N 33/44* (2006.01)
(Continued)

(52) U.S. Cl.
CPC ............ *C08K 5/092* (2013.01); *C08J 3/203* (2013.01); *C08J 11/04* (2013.01); *G01N 33/442* (2013.01);
(Continued)

(58) Field of Classification Search
CPC .. C08K 5/09; C08K 5/092; C08K 5/13; C08L 51/04; C08L 53/02; C08L 5/02; C08L 69/00
(Continued)

(56) References Cited

U.S. PATENT DOCUMENTS 2,835,648 A * 5/1958 Lappin .............. C08K 5/20
524/194
3,227,680 A * 1/1966 Tamblyn ............ C08G 63/16
528/128
(Continued)

FOREIGN PATENT DOCUMENTS

DE 102010042965 A1 5/2012
EP 0762917 B1 8/2001
(Continued)

OTHER PUBLICATIONS

"Recycled Content Standard, V7.0: Environmental Certification Services", SCS Global Services, downloaded from <http://www.scsglobalservices.com/files/standards/scs_stn_recycledcontent_v7-0_070814.pdf> on Dec. 15, 2014, 14 pages.
(Continued)

*Primary Examiner* — Jane L Stanley
(74) *Attorney, Agent, or Firm* — Matthew J. Bussan

(57) ABSTRACT

A composition for recyclate verification is produced by adding a predetermined quantity of one or more verification compounds to a base resin. Each of the verification compounds is thermally stable over a range of temperatures that includes the maximum processing temperature of the base resin but is less than the degradation temperature of the base resin. In some embodiments, a thermoplastic material provided for verification as a recyclate is analyzed to detect the presence (and, optionally, the loading level) of one or more verification compounds associated with the base resin of the thermoplastic material. In some embodiments, a computer-implemented method for recyclate verification is performed using a computer program product. In some embodiments, a thermoplastic material verified as a recyclate is heated to drive off the verification compound(s), then a known quan-
(Continued)

tity of the verification compound(s) is added to the recyclate, which is then blended with virgin base resin material.

4 Claims, 5 Drawing Sheets

(51) Int. Cl.
    *C08J 3/20* (2006.01)
    *C08J 11/04* (2006.01)
    *C08L 55/02* (2006.01)
(52) U.S. Cl.
    CPC ........ *C08J 2347/00* (2013.01); *C08J 2355/02* (2013.01); *C08J 2369/00* (2013.01); *C08J 2447/00* (2013.01); *C08J 2469/00* (2013.01); *C08L 55/02* (2013.01); *C08L 2666/02* (2013.01)
(58) Field of Classification Search
    USPC .......................................................... 524/321
    See application file for complete search history.

(56) References Cited

U.S. PATENT DOCUMENTS

| | | | | | |
|---|---|---|---|---|---|
| 3,673,129 | A | * | 6/1972 | Sagane | C08F 20/42 521/149 |
| 3,852,093 | A | * | 12/1974 | O'Leary | B41M 5/286 430/334 |
| 4,299,929 | A | * | 11/1981 | Sakano | C08K 5/09 524/112 |
| 5,201,921 | A | | 4/1993 | Luttermann et al. | |
| 5,256,880 | A | | 10/1993 | Loree et al. | |
| 5,329,127 | A | | 7/1994 | Becker et al. | |
| 5,420,181 | A | * | 5/1995 | Eichenauer | C08K 5/0008 524/100 |
| 5,626,240 | A | | 5/1997 | Friedrichs et al. | |
| 5,750,602 | A | * | 5/1998 | Kohler | C08L 51/04 524/123 |
| 5,811,036 | A | | 9/1998 | Takahashi et al. | |
| 6,423,767 | B1 | * | 7/2002 | Weber | C08K 5/092 524/158 |
| 8,450,382 | B2 | | 5/2013 | Riise et al. | |
| 2004/0242739 | A1 | | 12/2004 | Daute et al. | |
| 2005/0277710 | A1 | | 12/2005 | Joyce et al. | |
| 2009/0164318 | A1 | | 6/2009 | Hama | |
| 2014/0221528 | A1 | | 8/2014 | Ribi | |
| 2014/0278142 | A1 | | 9/2014 | Danes et al. | |
| 2014/0339726 | A1 | | 11/2014 | Guven | |
| 2015/0031837 | A1 | | 1/2015 | Favis et al. | |
| 2016/0200894 | A1 | | 7/2016 | Hebig et al. | |

FOREIGN PATENT DOCUMENTS

| | | | |
|---|---|---|---|
| EP | 1967294 | A2 | 9/2008 |
| GB | 2330409 | A | 4/1999 |
| WO | 9532780 | A2 | 12/1995 |
| WO | 2012109741 | A1 | 8/2012 |
| WO | 2013001101 | A1 | 1/2013 |
| WO | 2015144114 | A1 | 10/2015 |

OTHER PUBLICATIONS

"Recycled Content Program Certification Manual: Environmental Certification Services", SCS Global Services, downloaded from <http://www.scsglobalservices.com/files/resources/MC_RC_CertificationManual_V3-0_102212.pdf> on Dec. 15, 2014, 8 pages.
"Recycled Content: Certification for responsible manufacturing", SCS Global Services, downloaded from <http://www.scsglobalservices.com/files/brochures/COM_ECS_INF_Recycled_v2-1_071712.pdf> on Dec. 15, 2014, 2 pages.
U.S. Appl. No. 14/596,324, to Hebig et al., entitled "Recyclate Verification", filed Jan. 14, 2015, assigned to International Business Machines Corporation.
List of IBM Patents or Patent Applications Treated as Related.
List of IBM Patents of Patent Applications Treated as Related (updated Mar. 24, 2017).
U.S. Appl. No. 15/467,995, to Hebig et al., entitled "Recyclate Verification", filed Mar. 23, 2017, assigned to International Business Machines Corporation.
U.S. Appl. No. 15/468,026, to Hebig et al., entitled "Recyclate Verification", filed Mar. 23, 2017, assigned to International Business Machines Corporation.
Brunner et al., Automated sorting of polymer flakes: Fluorescence labeling and development of a measurement system prototype, Elsevier, www.elsevier.com/locate/wasman (online), Waste Management, 38, Available Online Jan. 28, 2015, 12 pages.
Langhals et al., Binary Fluorescence Labeling for the Recovery of Polymeric Materials for Recycling, International Journal of Environmental Engineering Science and Technology Research, vol. 1, No. 7, dated Jul. 2013, www.jestr.org, ISSN: 2326-3113 (Online), 9 pages.
Maris et al., Polymer tracer detection systems with UV fluorescence spectrometry to improve product recyclability, Elsevier, www.elsevier.com/locate/mineng (online), Minerals Engineering, 29, dated 2012, 12 pages.
Brunner et al., Investigation of Algorithms for the Reliable Classification of Fluorescently Labeled Plastics, Instrumentation and Measurement Technology Conference (I2MTC), dated 2012, IEEE Xplore Digital Library (online), 5 pages.
Dr. William Coyle, Anti-Counterfeiting Drug Initiative: Fluorescent Materials, http://www.fda.gov/ohrms/dockets/dailys/03/oct03/101503/03N-0361-emc-000002-01.doc (online), Submission Date: Oct. 8, 2003, 4 pages.
Lee et al., Photophysical properties of tris(bipyridyl)ruthenium(II) thin films and devices, PCCP, Physical Chemistry Chemical Physics, 2003, 5, 2706-2709, www.cosbkup.gatech.edu/group/PCCP-PaperFinalPublication.pdf (online), First published as an Advance Article on the web May 8, 2003, 4 pages.
EPEAT, Outcomes Report EPEAT Verification Round Four, http://www.epeat.net/documents/verification-round/2009-04/outcomes-report-2009-04.pdf (online), Dec. 2009, 6 pages.
Disclosed Anonymously, "Use of Taggants to Track Recycled Metal Content", An IP.com Prior Art Database Technical Disclosure, IPCOM000242349D, Jul. 9 2015, 3 pages.
List of IBM Patents or Patent Applications Treated as Related (updated Mar. 3, 2017).
U.S. Appl. No. 15/280,382, to Czaplewski, entitled "Fluorosphores for Recycled Content Verification", filed Sep. 29, 2016, assigned to International Business Machines Corporation.
Fent et al., "Assessment of uptake and toxicity of fluorescent silica nanoparticles in zerbrafish (Danio rerio) early life stages," Aquatic Toxicology, vol. 100, 2010, pp. 218-228.

\* cited by examiner

RECYCLATE VERIFICATION

CROSS-REFERENCE TO RELATED APPLICATION

This patent application is a continuation application of pending U.S. patent application Ser. No. 14/596,324, filed Jan. 14, 2015, entitled "RECYCLATE VERIFICATION", which is hereby incorporated herein by reference in its entirety.

BACKGROUND

The present invention relates in general to plastics recycling. More particularly, the present invention relates to a composition for recyclate verification that includes one or more verification compounds added to a base resin. The present invention also relates to a method for producing such a composition, as well as to a method and computer program product for verifying recyclate.

SUMMARY

In accordance with some embodiments of the present invention, a composition for recyclate verification is produced by adding a predetermined quantity of one or more verification compounds to a base resin. Each of the verification compounds is thermally stable over a range of temperatures that includes the maximum processing temperature of the base resin but is less than the degradation temperature of the base resin. In some embodiments of the present invention, a thermoplastic material provided for verification as a recyclate is analyzed to detect the presence (and, optionally, measure the loading level) of one or more verification compounds associated with the base resin of the thermoplastic material. In some embodiments of the present invention, a computer-implemented method for recyclate verification is performed using a computer program product. In some embodiments of the present invention, a thermoplastic material verified as a recyclate is heated to drive off the verification compound(s), then a known quantity of the verification compound(s) is added to the recyclate, which is then blended with virgin base resin material.

BRIEF DESCRIPTION OF THE SEVERAL VIEWS OF THE DRAWINGS

Embodiments of the present invention will hereinafter be described in conjunction with the appended drawings, where like designations denote like elements.

DETAILED DESCRIPTION

Figure 1:
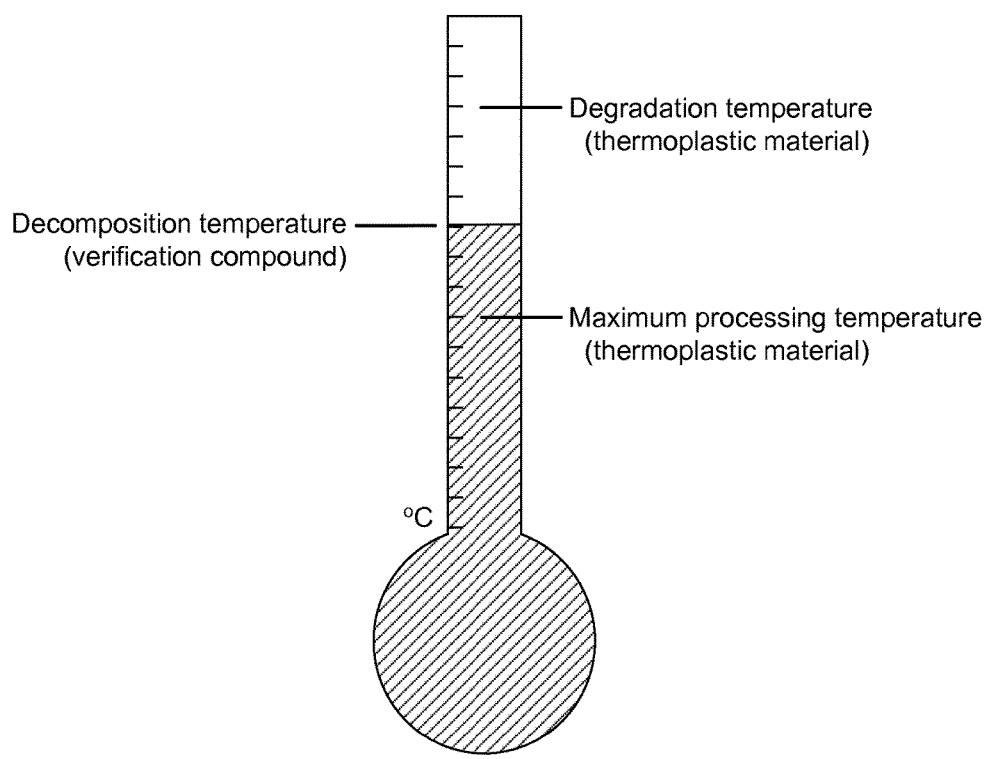
FIG. 1 is a conceptual temperature gauge diagram illustrating relationships between various thermal properties of a thermoplastic material and the thermal stability of a verification compound to be added to the thermoplastic material for recyclate verification in accordance with some embodiments of the present invention.

Recently, there is a greater focus on the use of recycled plastic in an attempt to minimize the quantity of virgin resin required for a given application. Recycled plastic is often blended with virgin material and sold at a premium (due to the logistics of collecting and sorting the recycled plastic). However, it is extremely difficult using conventional techniques to verify the recycled resin content in the resin blend because the recycled resin and the virgin resin are chemically identical. The only conventional method to verify the recycled resin content in the resin blend is via an extensive supply chain audit. Consequently, a need exists for a more practical mechanism for recyclate verification.

In accordance with some embodiments of the present invention, at least one verification compound is added to the recyclate that will indicate that it is recycled material. The recyclate is then blended with virgin base resin material. The indicator is thermally stable at the melt temperature of the resin but can be removed (thermally or otherwise) at higher temperature provided that the higher temperature is still below the decomposition temperature of the resin. When the material comes back to the compounder/recycler, it may be heated to drive off the indicator(s), then a known quantity of the verification compound(s) is added to the recyclate. The recyclate is then blended with the virgin base resin material. The resultant material can then be tested for the indicator.

In accordance with some embodiments of the present invention, a composition for recyclate verification is produced by adding a predetermined quantity of one or more verification compounds to a base resin. The predetermined quantity achieves a nominal loading level for each verification compound. The composition may comprise a set of two or more of the verification compounds. Each of the verification compounds is thermally stable over a range of temperatures that includes a maximum processing temperature of the base resin but is less than a degradation temperature of the base resin.

For purposes of this document, including the claims, the terminology "degradation temperature" refers to the lowest temperature at which the base resin begins to substantially degrade (e.g., the decomposition temperature of the base resin).

For purposes of this document, including the claims, the terminology "base resin" refers to a thermoplastic material. A thermoplastic material (sometimes referred to as a "thermosoftening plastic") is a plastic material that becomes pliable or moldable above a specific temperature (e.g., melting temperature (Tm), glass transition temperature (Tg), Vicat softening temperature (VST), and the like) and solidifies upon cooling. Thermoplastic materials typically comprise one or more polymers. Suitable base resins include, but are not limited to, polyethylene terephthalate (PET or PETE) (often identified by the resin identification code (RIC) number "1"), high-density polyethylene (HDPE or PE-HD) (often identified by the RIC number "2"), polyethylene chloride (PVC) (often identified by the RIC number "3"), low-density polyethylene (LDPE or PE-LD) (often identified by the RIC number "4"), polypropylene (PP) (often identified by the RIC number "5"), polystyrene (PS) (often identified by the RIC number "6"), polycarbonate (PC), acrylonitrile butadiene styrene (ABS), and blends thereof "Other" types of plastic, such as PC and ABS, are often identified by the RIC number "7".

FIG. 1 is a conceptual temperature gauge diagram illustrating relationships between various thermal properties of a thermoplastic material (e.g., the maximum processing temperature of the thermoplastic material, as well as the degradation temperature of the thermoplastic material) and the thermal stability of a verification compound to be added to the thermoplastic material for recyclate verification in accordance with some embodiments of the present invention. As illustrated in FIG. 1, the decomposition temperature (e.g., boiling point, sublimation temperature, etc.) of the verification compound is between the maximum processing temperature of the base resin and the degradation temperature (e.g., decomposition temperature) of the base resin. In other words, the verification compound is thermally stable over a range of temperatures that includes the maximum processing temperature of the base resin but is less than the degradation temperature of the base resin. Generally, any organic compound that satisfies these relationships is suitable for use as a verification compound.

Organic compounds that may be suitable for use as a verification compound (depending on the base resin) include, but are not limited to, medium or long chain, mono- or di-carboxylic acids (e.g., glutaric acid, adipic acid, pimelic acid, suberic acid, azelaic acid, sebacic acid, linoleic acid, hexanoic acid (also referred to as "caproic acid"), caprylic acid, lauric acid, myristic acid, palmitic acid, stearic acid, and pelargonic acid) and mono-, di-, or tri-hydroxy-benzoic acids (e.g., 2-hydroxybenzoic acid (also referred to as "salicylic acid"), 2-5-dihydroxybenzoic acid (also referred to as "gentisic acid"), 3,4-dihydroxybenzoic acid (also referred to as "protocatechuic acid"), and ethyl protocatechuate).

In some embodiments of the present invention, a thermoplastic material provided for verification as a recyclate is analyzed to detect the presence (and, optionally, measure the loading level) of one or more verification compounds associated with the base resin of the thermoplastic material. In some embodiments of the present invention, a computer-implemented method for recyclate verification is performed using a computer program product. In some embodiments of the present invention, a thermoplastic material verified as a recyclate is heated to drive off the verification compound(s), then a known quantity of the verification compound(s) is added to the recyclate, which is then blended with virgin base resin material.

Preferably, the loading level of each the one or more verification compounds within the recyclate is low so as not to adversely impact the chemical and/or physical properties of the base resin. For example, the loading level of each of the one or more verification compounds within the recyclate may be less than 1 wt %, preferably less than 0.1 wt %, and more preferably 0.01 wt %.

On one hand, some or all of the verification compound(s) and/or loading level(s) to be used in particular base resins may be made known to the public through, for example, standards organizations. On the other hand, some or all of the verification compound(s) and/or loading level(s) to be used in particular base resins may be kept secret (e.g., made known only to authorized compounders/recyclers).

Depending on the thermoplastic material to be molded, suitable organic compounds for use as the one or more verification compounds may be selected from a variety of material classes. By way of example, the injection molding process temperatures used for a PC/ABS blend base resin (i.e., a blend of polycarbonate (PC) and acrylonitrile butadiene styrene (ABS) as the base resin) include various barrel temperatures (e.g., the rear section (hopper) temperature of approximately 225-260° C., the intermediate section temperature of approximately 250-275° C., and the front section temperature of approximately 250-280° C.), the nozzle temperature of approximately 250-275° C., and the mold temperature of approximately 50-80° C. Hence, in this PC/ABS blend base resin example, the maximum processing temperature to which the PC/ABS blend is subjected to during the injection molding process is 280° C. In accordance with some embodiments of the present invention, selection of the one or more verification compounds is tailored for the thermoplastic material to be molded so that each verification compound is thermally stable at temperatures up to such a maximum processing temperature for the thermoplastic material to be molded. Consequently, in this PC/ABS blend base resin example, the verification compound(s) must be thermally stable at temperatures up to 280° C.

The maximum processing temperature for a given thermoplastic material to be molded is typically above the melting point of that thermoplastic material but is typically well below the degradation temperature of that thermoplastic material. Due to the amorphous nature of PC/ABS blends, this particular thermoplastic material does not display a melting point. Instead, the maximum processing temperature for the PC/ABS blend in this example is driven by other thermal properties of the PC/ABS blend. For example, the PC/ABS blend in this example has a glass transition temperature (Tg) of approximately 125° C., a Vicat softening temperature (VST) (B50 method) of approximately 112° C., and heat deflection temperatures (HDTs) at 66 psi and 264 psi of approximately 110° C. and 96° C., respectively. The maximum processing temperature (i.e., 280° C.) in this example is well above each of those temperatures. The degradation temperature for PC/ABS blends is approximately 400° C.

Therefore, in this PC/ABS blend base resin example, organic compounds suitable for use as a verification compound are thermally stable at 280° C. yet decompose below 400° C. A suitable class of organic compounds for use as a verification compound, at least with respect to this PC/ABS blend base resin example, is the long chain, mono- or di-carboxylic acids such as azelaic acid or sebacic acid. The respective chemical structures of azelic acid and sebacic acid are shown below:

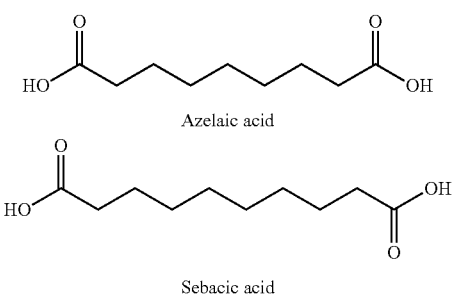

Azelaic acid

Sebacic acid

Azelaic acid has a melting point of approximately 109-111° C. and a boiling point of approximately 286° C. Azelaic acid has a carbon chain that is relatively long (i.e., nine carbon atoms in length). Sebacic acid has a melting point of approximately 131-134.5° C. and a boiling point of approximately 294° C. Sebacic acid has a carbon chain that is even longer (i.e., ten carbon atoms in length) than the carbon chain of azelaic acid. Thus, azelaic acid and/or sebacic acid are thermally stable at temperatures up to and exceeding 280° C. (i.e., the maximum processing temperature of the PC/ABS blend) yet decompose completely (i.e., volatilize) well below 400° C. (i.e., the decomposition temperature of the PC/ABS blend). It is possible, therefore, to drive off azelaic acid and/or sebacic acid added to a PC/ABS blend base resin (i.e., the PC/ABS blend base resin and the azelaic acid and/or the sebacic acid together constituting "recyclate") as verification compound(s) by heating the recyclate to a temperature beyond the boiling point of the verification compound(s) but short of the decomposition of the PC/ABS blend base resin. Moreover, azelaic acid and sebacic acid added to a PC/ABS blend base resin can be easily titrated in order to quantify the loading level of the verification compound(s) within the recyclate.

Suberic acid, on the other hand, is a long chain, di-carboxylic acid that is not suitable for use as a verification compound (at least not with respect to this PC/ABS blend base resin example). The chemical structure of suberic acid is shown below:

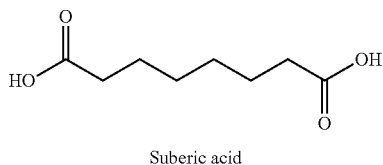 [SMILES: O=C(O)CCCCCCC(=O)O]

Suberic acid

Suberic acid has a melting point of approximately 141-144° C. and a boiling point of approximately 230° C. Thus, suberic acid is not thermally stable at temperatures up to 280° C. (i.e., the maximum processing temperature of the PC/ABS blend). Suberic acid has a carbon chain that is shorter (i.e., eight carbon atoms in length) than the carbon chains of azelaic acid and sebacic acid, thus making this particular long chain, di-carboxylic acid unsuitable for use as a verification compound in this particular base resin. That is, the shorter carbon chain makes the suberic acid too volatile for use as a verification compound (at least with respect to this PC/ABS blend base resin example).

Depending on the base resin used in the thermoplastic, different verification compound(s) may be utilized. For example, 2-5-dihydroxybenzoic acid, which sublimes at a temperature of approximately 200-205° C., may be used for ABS base resin (which typically has a maximum processing temperature of about 175° C. and a decomposition temperature of about 280° C.). The chemical structure of 2-5-dihydroxybenzoic acid is shown below:

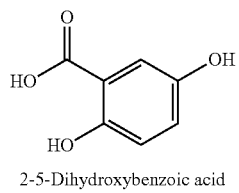 [SMILES: O=C(O)c1cc(O)ccc1O]

2-5-Dihydroxybenzoic acid

As mentioned above, 2-5-dihydroxybenzoic acid sublimes at a temperature of approximately 200-205° C. Thus, 2-5-dihydroxybenzoic acid is thermally stable at temperatures up to and exceeding 175° C. (i.e., the maximum processing temperature of the ABS base resin) yet decomposes completely (i.e., volatilizes by sublimation) well below 280° C. (i.e., the decomposition temperature of the ABS base resin). It is possible, therefore, to drive off 2-5-dihydroxybenzoic acid added to an ABS base resin (i.e., the ABS base resin and the 2-5-dihydroxybenzoic acid together constituting "recyclate") as a verification compound by heating the recyclate to a temperature beyond the sublimation temperature of the verification compound but short of the decomposition of the ABS base resin. Moreover, 2-5-dihydroxybenzoic acid added to an ABS base resin can be easily titrated in order to quantify the loading level of the verification compound within the recyclate.

Figure 2:
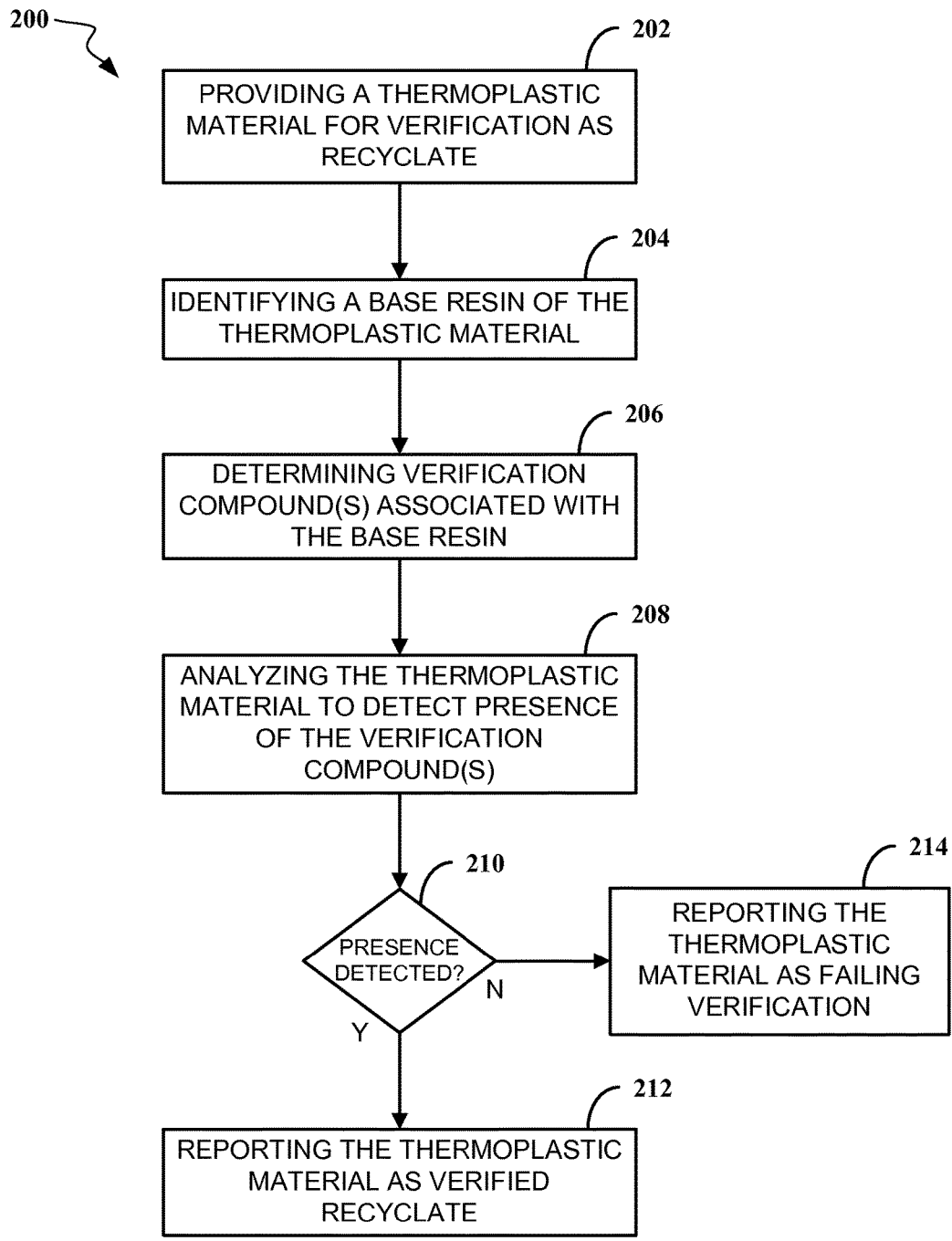
FIG. 2 is a flow diagram illustrating a method for verifying recyclate based on detection of the presence of one or more verification compounds in a thermoplastic material in accordance with some embodiments of the present invention.

FIG. 2 illustrates a flow diagram of a method 200 for verifying recyclate based on detection of the presence of one or more verification compounds in a thermoplastic material in accordance with some embodiments of the present invention. In the method 200, the steps discussed below (steps 202-214) are performed. These steps are set forth in their preferred order. It must be understood, however, that the various steps may occur at different times relative to one another than shown, or may occur simultaneously. Moreover, those skilled in the art will appreciate that one or more of the steps may be omitted.

The method 200 begins by providing a thermoplastic material for verification as recyclate (step 202). For example, a thermoplastic material may be provided by a conventional automatic sort system to a near-infrared (NIR) spectroscopy unit that automatically identifies the base resin in the thermoplastic material. Alternatively, the thermoplastic material may be provided to a human who manually identifies the base resin in the thermoplastic material using, for example, the RIC labeling system.

The method 200 continues by identifying the base resin in the thermoplastic material (step 204). For example, a near-infrared (NIR) spectroscopy unit may be used to identify the base resin in the thermoplastic material by irradiating the thermoplastic material with near-infrared light, measuring the absorption spectrum of the reflected near-infrared light, and comparing the measured absorption spectrum against reference absorption spectrum of known base resins. Alternatively, a human may manually identify the base resin in the thermoplastic material by reading a RIC label printed on the thermoplastic material.

Then, the method 200 continues by determining one or more verification compounds associated with the base resin identified in step 204 (step 206). For example, a recyclate verification application 535 (shown in FIG. 5) may access data files 540 (shown in FIG. 5) to automatically determine the verification compound(s) associated with the base resin identified in step 204. The data files 540 may, for each of any number of base resins, list one or more verification compounds that is/are associated with that particular base resin. Alternatively, a human may access the data files 540 or the like to manually determine the verification compound(s) associated with the base resin identified in step 204.

The method 200 then continues by analyzing the thermoplastic material to detect the presence of the one or more verification compounds determined in step 206 (step 208). For example, an automatic chemical analysis system (e.g., a conventional automatic assay system) may be used to automatically detect the presence of the verification compound(s) in the thermoplastic material. Alternatively, a human may manually detect the presence of the verification compound(s) in the thermoplastic material (e.g., via any suitable assay technique known to those skilled in the art).

Then, the method 200 continues by determining whether the presence of the one or more verification compounds determined in step 206 was detected when the thermoplastic material was analyzed in step 208 (step 210). If each of the verification compound(s) was detected (step 210=Yes), the method 200 continues by reporting the thermoplastic material as verified recyclate (step 212). On the other hand, if each of the verification compound(s) was not detected (step 210=No), the method 200 continues by reporting the thermoplastic material as failing verification (step 214).

Figure 3:
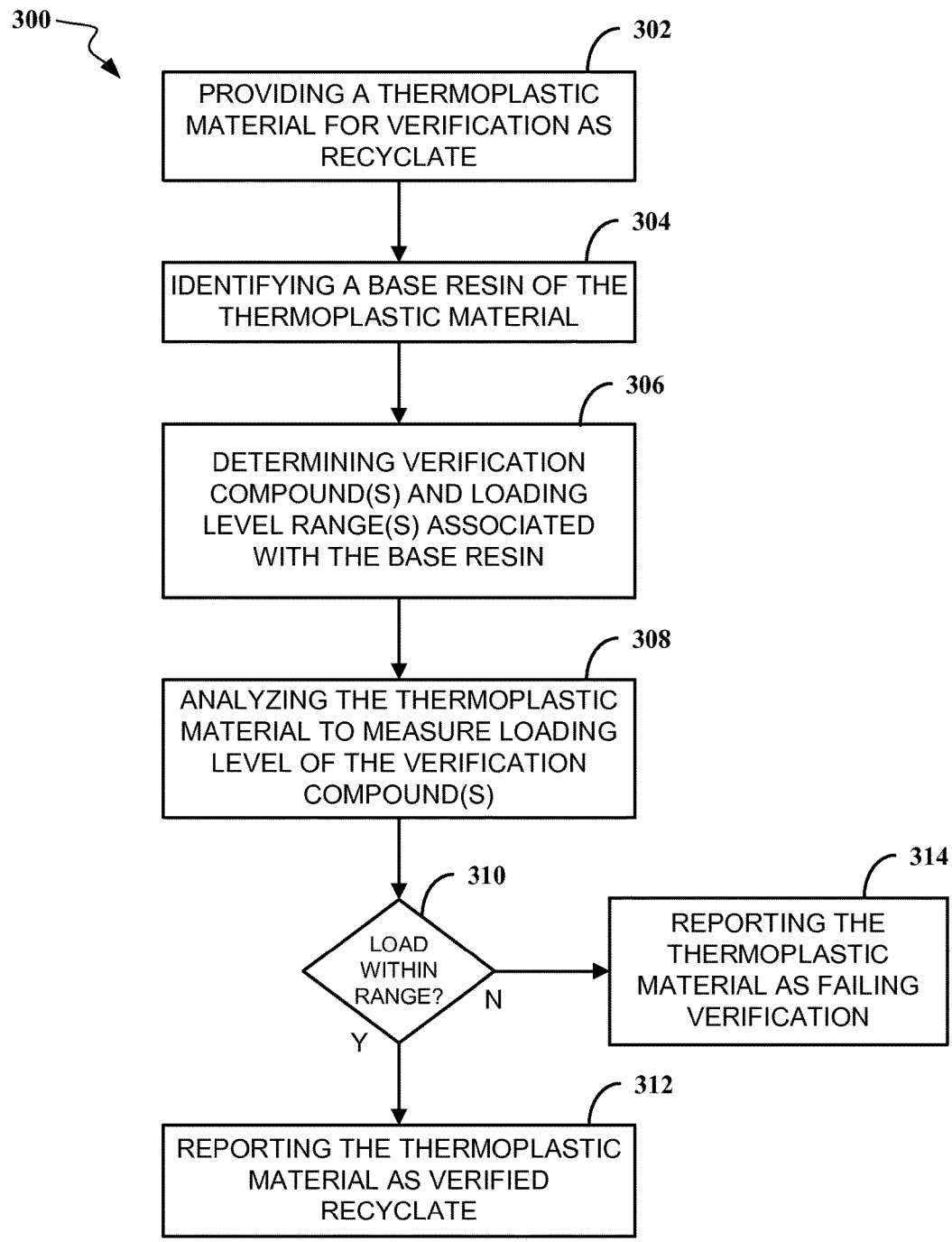
FIG. 3 is a flow diagram illustrating a method for verifying recyclate based on measurement of the loading level of one or more verification compounds in a thermoplastic material in accordance with some embodiments of the present invention.

FIG. 3 illustrates a flow diagram of a method 300 for verifying recyclate based on measuring of the loading level of one or more verification compounds in a thermoplastic material in accordance with some embodiments of the present invention. In the method 300, the steps discussed below (steps 302-314) are performed. These steps are set forth in their preferred order. It must be understood, however, that the various steps may occur at different times relative to one another than shown, or may occur simultaneously. Moreover, those skilled in the art will appreciate that one or more of the steps may be omitted.

The method 300 begins by providing a thermoplastic material for verification as recyclate (step 302). For example, a thermoplastic material may be provided by a conventional automatic sort system to a near-infrared (NIR) spectroscopy unit that automatically identifies the base resin in the thermoplastic material. Alternatively, the thermoplastic material may be provided to a human who manually identifies the base resin in the thermoplastic material using, for example, the RIC labeling system.

The method 300 continues by identifying the base resin in the thermoplastic material (step 304). For example, a near-infrared (NIR) spectroscopy unit may be used to identify the base resin in the thermoplastic material by irradiating the thermoplastic material with near-infrared light, measuring the absorption spectrum of the reflected near-infrared light, and comparing the measured absorption spectrum against reference absorption spectrum of known base resins. Alternatively, a human may manually identify the base resin in the thermoplastic material by reading a RIC label printed on the thermoplastic material.

Then, the method 300 continues by determining one or more verification compounds and loading level range(s) associated with the base resin identified in step 304 (step 306). For example, a recyclate verification application 535 (shown in FIG. 5) may access data files 540 (shown in FIG. 5) to automatically determine the verification compound(s) and loading level range(s) associated with the base resin identified in step 304. The data files 540 may, for each of any number of base resins, list one or more verification compounds that is/are associated with that particular base resin, along with a loading level range for each of the one or more verification compounds. Each loading level range provides a suitable tolerance above and below a nominal loading level for a particular verification compound. Alternatively, a human may access the data files 540 or the like to manually determine the verification compound(s) and loading level range(s) associated with the base resin identified in step 304.

The method 300 then continues by analyzing the thermoplastic material to measure the loading level for each of the one or more verification compounds determined in step 306 (step 308). For example, an automatic chemical analysis system (e.g., a conventional automatic titration system) may be used to automatically measure the loading level of the verification compound(s) in the thermoplastic material. Alternatively, a human may manually measure the loading level of the verification compound(s) in the thermoplastic material (e.g., via any suitable titration technique known to those skilled in the art).

Then, the method 300 continues by determining whether the loading level for each of the one or more verification compounds measured when the thermoplastic material was analyzed in step 308 was within a corresponding one of the one or more loading level ranges determined in step 306 (step 310). If the measured loading level for each of the verification compound(s) was within the corresponding loading level range (step 310=Yes), the method 300 continues by reporting the thermoplastic material as verified recyclate (step 312). If the measured loading level for each of the verification compound(s) was not within the corresponding loading level range (step 310=No), the method 300 continues by reporting the thermoplastic material as failing verification (step 314).

Figure 4:
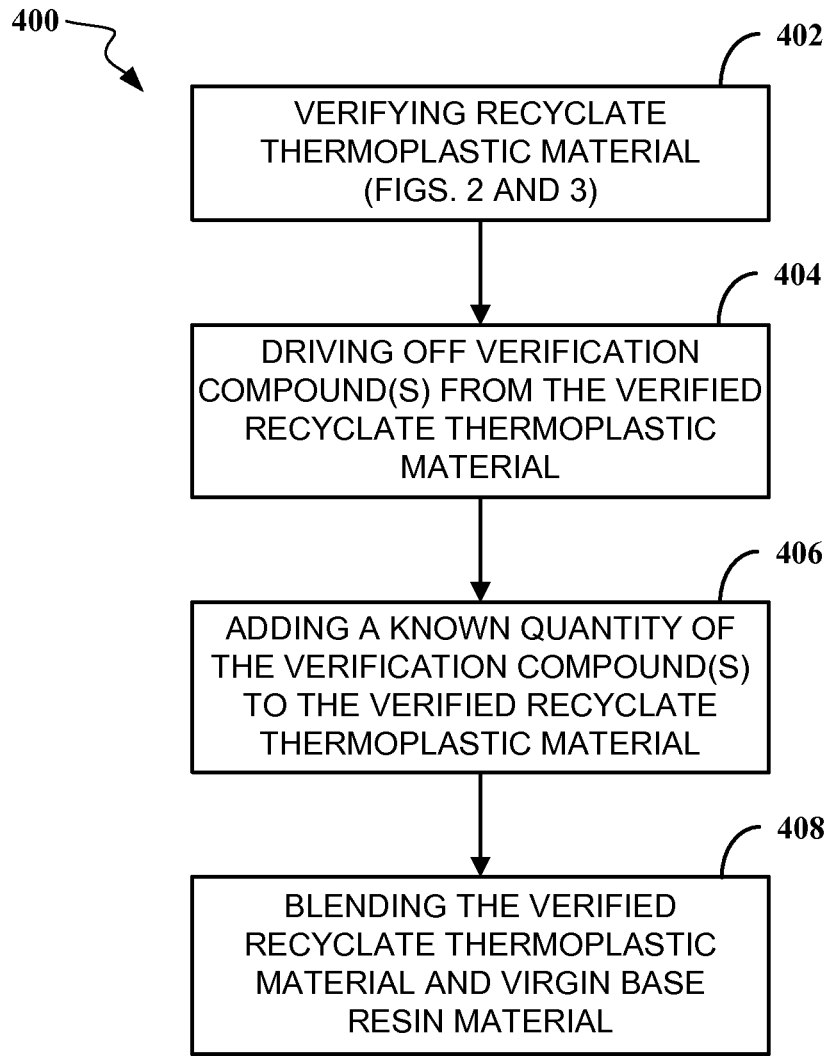
FIG. 4 is a flow diagram illustrating a method for verifying recyclate in which verified recyclate thermoplastic material is blended with virgin base resin material in accordance with some embodiments of the present invention.

FIG. 4 illustrates a flow diagram of a method 400 for verifying recyclate in which verified recyclate thermoplastic material is blended with virgin base resin material in accordance with some embodiments of the present invention. In the method 400, the steps discussed below (steps 402-408) are performed. These steps are set forth in their preferred order. It must be understood, however, that the various steps may occur at different times relative to one another than shown, or may occur simultaneously. Moreover, those skilled in the art will appreciate that one or more of the steps may be omitted.

The method 400 begins by verifying recyclate thermoplastic material (step 402). Step 402 may, for example, correspond to performing the method 200 (shown in FIG. 2) or the method 300 (shown in FIG. 3), where the thermoplastic material is reported as verified recyclate (i.e., step 212 or step 312).

The method 400 continues by driving off the verification compound(s) from the verified recyclate thermoplastic material (step 404). For example, the verified recyclate thermoplastic material may be heated to the decomposition temperature of the verification compound(s).

Then, the method 400 continues by adding a known quantity of the verification compound(s) to the verified recyclate thermoplastic material (step 406). For example, the known quantity of the verification compound(s) added to the verified recyclate thermoplastic material in step 406 may be determined to provide a nominal loading level for each verification compound in a blend that will comprise both the verified recyclate thermoplastic material and virgin base resin material.

The method 400 then continues by blending the verified recyclate thermoplastic material having the known quantity of the verification compound(s) added thereto in step 406 and the virgin base resin material (step 408).

Figure 5:
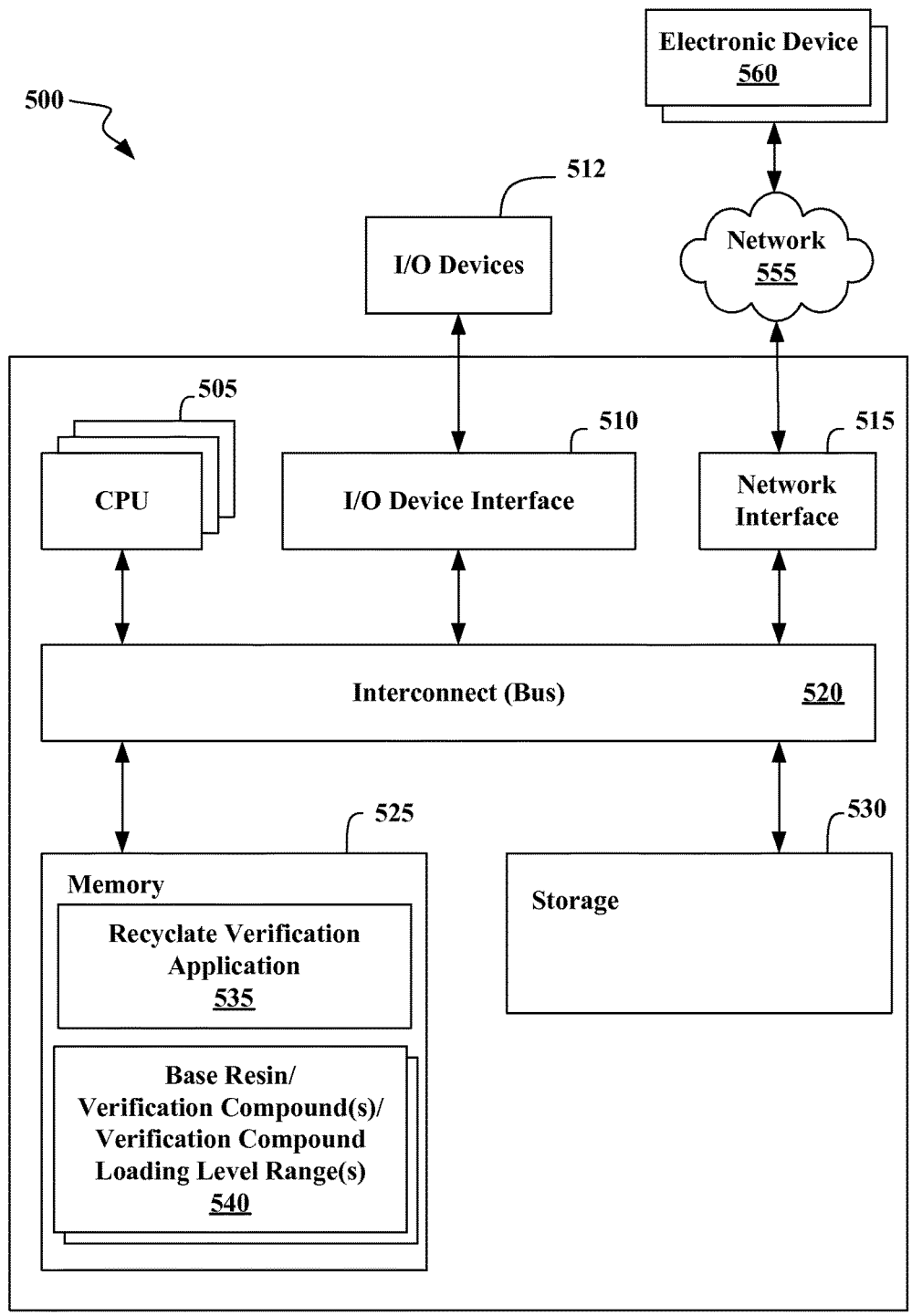
FIG. 5 is a block diagram illustrating an exemplary representation of a computer system for performing a computer-implemented method for recyclate verification in accordance with some embodiments of the present invention.

FIG. 5 illustrates an exemplary representation of a computer system 500 connected to one or more electronic devices 560 (e.g., an embedded controller of one or more automatic sort systems to identify the base resin in the recyclate, such as a conventional automatic sort system that utilizes near-infrared (NIR) spectroscopy, and/or one or more automatic chemical analysis systems to detect the presence/loading level of one or more verification compounds in the recyclate, such as a conventional automatic assay system or a conventional automatic titration system) via a network 555, for performing a computer-implemented method for recyclate verification in accordance with some embodiments of the present invention. For the purposes of this disclosure, computer system 500 may represent practically any type of computer, computer system, or other programmable electronic device, including but not limited to, a client computer, a server computer, a portable computer, a handheld computer, an embedded controller, etc. In some embodiments, computer system 500 may be implemented using one or more networked computers, e.g., in a cluster or other distributed computing system.

The computer system 500 may include, without limitation, one or more processors (CPUs) 505, a network interface 515, an interconnect 520, a memory 525, and storage 530. The computer system 500 may also include an I/O device interface 510 used to connect I/O devices 512, e.g., keyboard, display, and mouse devices, to the computer system 500.

Each processor 505 may retrieve and execute programming instructions stored in the memory 525 or storage 530. Similarly, the processor 505 may store and retrieve application data residing in the memory 525. The interconnect 520 may transmit programming instructions and application data between each processor 505, I/O device interface 510, network interface 515, memory 525, and storage 530. The interconnect 520 may be one or more busses. The processor 505 may be a single central processing unit (CPU), multiple CPUs, or a single CPU having multiple processing cores in various embodiments. In one embodiment, a processor 505 may be a digital signal processor (DSP).

The memory 525 may be representative of a random access memory, e.g., Static Random Access Memory (SRAM), Dynamic Random Access Memory (DRAM), read-only memory, or flash memory. The storage 530 may be representative of a non-volatile memory, such as a hard disk drive, solid state device (SSD), or removable memory cards, optical storage, flash memory devices, network attached storage (NAS), or connections to storage area network (SAN) devices, or other devices that may store non-volatile data. The network interface 515 may be configured to transmit data via the communications network 555.

The memory 525 may include a recycle verification application 535, one or more data files denoted in FIG. 5 as "base resin/verification compound(s)/verification compound loading level range(s) 540". Although these elements are illustrated as residing in the memory 525, any of the elements, or combinations thereof, may reside in the storage 530 or partially in the memory 525 and partially in the storage 530. The data files 540 may also reside, at least partially, in a data base (not shown) which the computer system 500 may access through the network 555. The recycle verification application 535 has a set (at least one) of program modules that, in conjunction with the one or more data files 540, one or more automatic sort systems to identify the base resin in the recycle (e.g., a conventional automatic sort system that utilizes near-infrared (NIR) spectroscopy), and one or more automatic chemical analysis systems to detect the presence/loading level of one or more verification compounds in the recycle (e.g., a conventional automatic assay system or a conventional automatic titration system), generally carry out the functions and/or methodologies of embodiments of the invention as described herein.

The network 555 may be any suitable network or combination of networks and may support any appropriate protocol suitable for communication of data and/or code to/from the computer system 500 and the electronic device 560. In some embodiments, the network 555 may support wireless communications. In other embodiments, the network 555 may support hardwired communications. The network 555 may be the Internet and may support Internet Protocol in some embodiments. In other embodiments, the network 555 may be implemented as a local area network (LAN) or a wide area network (WAN). The network 555 may also be implemented as a cellular data network. Although the network 555 is shown as a single network in the figures, one or more networks of the same or different types may be included.

As shown, there may be one or more electronic devices 560 connected to the computer system 500 via the network 555. The electronic device 560 may include some or all of the hardware and software elements of the computer system 500 previously described. For the purposes of this disclosure, the electronic device 560 may represent practically any type of computer, computer system, or other programmable electronic device, including but not limited to, a client computer, a server computer, a portable computer, a handheld computer, an embedded controller, etc.

The present invention may be a composition, a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

One skilled in the art will appreciate that many variations are possible within the scope of the present invention. Thus, while the present invention has been particularly shown and described with reference to preferred embodiments thereof, it will be understood by those skilled in the art that these and other changes in form and details may be made therein without departing from the spirit and scope of the present invention.

What is claimed is:

1. A composition for recyclate verification, comprising:
a base resin, wherein the base resin is capable of being injection molded at a maximum processing temperature, and wherein the base resin is acrylonitrile butadiene styrene (ABS);
one or more verification compounds added to the base resin to achieve a nominal loading level of less than 0.1% by weight for each of the one or more verification compounds, wherein each of the one or more verification compounds is thermally stable over a range of temperatures that includes the maximum processing temperature but is less than a degradation temperature of the base resin, and wherein the one or more verification compounds comprises 2,5-dihydroxybenzoic acid.

2. The composition as recited in claim 1, wherein the nominal loading level of the 2,5-dihydroxybenzoic acid is 0.01 wt %.

3. A composition for recyclate verification, comprising:
a base resin comprising acrylonitrile butadiene styrene (ABS);
one or more verification compounds added to the base resin to achieve a nominal loading level of less than 0.1% by weight for each of the one or more verification compounds, wherein the one or more verification compounds comprises 2,5-dihydroxybenzoic acid.

4. The composition as recited in claim 3, wherein the nominal loading level of the 2,5-dihydroxybenzoic acid is 0.01 wt %.

* * * * *